(12) United States Patent
Hui et al.

(10) Patent No.: US 7,525,724 B2
(45) Date of Patent: Apr. 28, 2009

(54) LASER SYSTEM FOR PHOTONIC EXCITATION INVESTIGATION

(75) Inventors: Rongqui Hui, Lawrence, KS (US); Carey K. Johnson, Lawrence, KS (US)

(73) Assignee: The University of Kansas, Lawrence, KS (US)

( * ) Notice: Subject to any disclaimer, the term of this patent is extended or adjusted under 35 U.S.C. 154(b) by 42 days.

(21) Appl. No.: 11/687,162

(22) Filed: Mar. 16, 2007

(65) Prior Publication Data

US 2007/0215816 A1  Sep. 20, 2007

Related U.S. Application Data (60) Provisional application No. 60/783,010, filed on Mar. 16, 2006.

(51) Int. Cl.
*G02F 1/35* (2006.01)
*G01J 3/44* (2006.01)

(52) U.S. Cl. ........................ 359/326; 359/327; 356/301; 356/309

(58) Field of Classification Search ................. 359/326, 359/327; 356/301, 309, 310, 311, 316, 456; 385/122

See application file for complete search history.

(56) References Cited

U.S. PATENT DOCUMENTS

| 5,034,613 | A | 7/1991 | Denk | |
|---|---|---|---|---|
| 6,236,779 | B1 * | 5/2001 | Kafka et al. | 385/31 |
| 2005/0226278 | A1 * | 10/2005 | Gu et al. | 372/6 |
| 2007/0272838 | A1 * | 11/2007 | Kudo et al. | 250/227.12 |
| 2008/0059135 | A1 * | 3/2008 | Murugkar et al. | 703/11 |
| 2008/0081950 | A1 * | 4/2008 | Koenig et al. | 600/160 |

OTHER PUBLICATIONS

Jay Unruh, E. Shane Price, Roque Gagliano Molla, Lisa Stehno-Bittel, Carey K. Johnson, and Rongqing Hui, Two-photon Microscopy with Wavelength Switchable Fiber Laser Excitation, Optics Express 9825, Oct. 16, 2006, vol. 14, No. 21.

(Continued)

*Primary Examiner*—Hemang Sanghavi
(74) *Attorney, Agent, or Firm*—Spencer Fane Britt & Browne LLP (57) ABSTRACT

A laser system (10) for use in photonic excitation investigation of a target object, in which the target object interacts with incident photons and emits a corresponding photon which is detected and used to generate an image of the target object. The laser system (10) includes a pulsed fiber laser (14) for producing a laser beam, and a non-linear photonic crystal fiber (16) for carrying the laser beam from the laser (14) to an instrument (18) for photonically exciting the target object. The photonic crystal fiber (16) allows for switching, or tuning, the wavelength of the laser beam. In two-photon microscopy, the laser system (10) allows for providing multiple wavelengths for exciting a plurality of different fluorophores simultaneously. In coherent Raman imaging and spectroscopy, the laser system (110) allows for using a single laser to provide two laser beams of different wavelengths.

8 Claims, 8 Drawing Sheets

OTHER PUBLICATIONS

Roque Gagliano Molla, Nonlinear Fiber Optics for Bio-Imaging, May 20, 2005.

Esben Ravn Andresen, Victoria Birkedal, Jan Thogersen, Soren Rud Keiding, Tunable Light source for coherent anti-Stokes Raman scattering microspectroscopy based on the soliton self-frequency shift; Optics Letters, vol. 31, No. 9, May 1, 2006, pp. 1328-1330.

Esben Ravn Andresen, Carsten Krogh Nielsen, Jan Thogersen, Soren Rud Keiding; "Fiber laser-based light source for coherent anti-Stokes Raman scattering microspectorscopy"; Optics Express, Apr. 16, 2007, vol. 15, No. 8, pp. 4848-4856.

Esben Ravn Andresen, Henrik Norgaard Paulsen, Victoria Birkedal, Jan Thogersen, Soren Rud Keiding, "Broadband multiplex coherent anti-Stokes Raman scattering microscopy employing photonic-crystal fibers"; Optical Society of America, B/vol. 22, No. 9, Sep. 2005, pp. 1934-1938.

* cited by examiner

FIG. 9

LASER SYSTEM FOR PHOTONIC EXCITATION INVESTIGATION

RELATED APPLICATIONS

The present non-provisional patent application claims priority benefit of an earlier-filed provisional patent application titled "Wavelength Tunable Femtosecond Laser Source for Two-Photon Biological Imaging and Correlated Antistocks Raman Spectrosco", Ser. No. 60/783,010, filed Mar. 16, 2006. The identified earlier-filed application is hereby incorporated by reference into the present application.

FIELD OF THE INVENTION

The present invention relates to laser systems for use in photonic excitation investigation, particularly microscopy and spectroscopy, of a target object. More specifically, the present invention concerns such a laser system comprising a pulsed fiber laser and a non-linear photonic crystal fiber, wherein the photonic crystal fiber allows for switching, or tuning, the wavelength of the laser beam, for use in, for example, two-photon microscopy and coherent Raman imaging and spectroscopy, including Coherent Anti-Stokes Raman Scattering.

BACKGROUND OF THE INVENTION

It is often desirable to investigate small objects, such as biological tissues and chemical molecules. To that end, photonic excitation has application in both microscopy and spectroscopy. Broadly, the target object interacts with incident photons and emits a corresponding photon which is detected and used to generate an image of the target object.

Two-photon excitation microscopy involves the simultaneous absorption by a fluorophore of two photons of relatively low energy, causing emission by the fluorophore of a single fluorescence photon. More specifically, an intrinsic fluorophore or a fluorescent dye attached to the target is excited by the incident photons and emits the fluorescent photon which can be used to produce an image of the target. This technology allows for deeper penetration and higher resolution than conventional confocal microscopy.

The probability of simultaneous absorption of two photons is relatively low but increases quadratically with excitation intensity. As such, a strongly focused, subpicosecond pulse laser is typically used as the source of excitation photons. Scanning the laser beam allows for collecting two-photon excited fluorescence from multiple points on the target, from which a comprehensive image of the target can be constructed. The highly localized character of two-photon excitation and the use of near-infrared wavelengths minimize damage to the target and reduce the autofluorescent background noise experienced in confocal microscopy. Unfortunately, applications for two-photon microscopy have been limited by the requirement of using a relatively large and expensive solid state laser, such as a Ti:Sapphire laser, as the source of excitation photons. Furthermore, wavelength switching with a solid state laser requires mechanical realignment of the laser and can be difficult to accomplish.

Coherent Raman imaging and spectroscopy exploits the Raman effect in which incident light is scattered at a wavelength shifted by the energy of a molecular vibration, either to lower energy (longer wavelength) in Stokes Raman scattering or to higher energy (shorter wavelength) in anti-Stokes Raman scattering.

Coherent Anti-Stokes Raman Scattering (CARS) involves the nonlinear conversion of two laser beams into a coherent Raman beam of high intensity in the anti-Stokes region. The resulting emission is stronger than normal Raman scattering because of coherent interaction of light with the sample. This technique allows for obtaining high-quality three-dimensional images. CARS does not require fluorescent labeling of the target object; instead, different molecules are identified by the strengths and wavelengths of the emitted Anti-Stokes light. Unfortunately, CARS imaging and spectroscopy require the use of two different and expensive laser sources, such as two Ti:Sapphire lasers, which must be stringently synchronized and maintained. Such synchronization is particularly difficult because the widths of the optical pulses are on the order of 100 femtoseconds, i.e., $100 \times 10^{-15}$ seconds.

SUMMARY OF THE INVENTION

The present invention overcomes the above-discussed and other problems in the prior art by providing an improved laser system for use in photonic excitation investigation of a target object. In one embodiment, the laser system comprises a pulsed fiber laser and a non-linear photonic crystal fiber, wherein the photonic crystal fiber allows for switching, or tuning, the wavelength of the laser beam prior to providing it to an instrument for photonically exciting the target object. The target object absorbs the incident photons, and emits a corresponding photon which is detected and used to generate an image of the target object.

In one embodiment, the laser system is incorporated into a system for performing two-photon excitation microscopy on the target object. The system comprises the laser system; a two-photon excitation microscope operable to receive the laser beam from the PCF, and including a scanning stage operable to move the target object or a beam scanner to scan the excitation light so as to expose a larger area of the target object to the laser beam, and further including a detector operable to detect a fluorescence photon emitted by the target object in response to absorption of the laser light and to generate an electronic signal corresponding thereto; and a signal processing component operable to produce or facilitate producing an image of the target object based upon the electronic signal generated by the detector. The PCF is operable to switch the wavelength of the laser beam so as to provide a plurality of wavelengths to the two-photon excitation microscope. In one embodiment, these wavelengths are approximately between 810 nm and 1100 nm, i.e., the near-infrared region.

In another embodiment, the laser system is incorporated into a system for performing coherent Raman scattering (e.g., CARS) on the target object. The laser system comprises the pulsed fiber laser operable to produce an output laser beam; a beam splitter operable to split the output laser beam into a first laser beam and a second laser beam; a first path operable to carry the first laser beam; a second path operable to carry the second laser beam, the second path including the PCF operable to shift a wavelength of the second laser beam; and a beam combiner operable to recombine the first laser beam and the second laser beam prior to providing them to the spectroscope. In one embodiment, the first path introduces an optical delay to the first laser beam to match the delay introduced by wavelength shifting in the second path. In one embodiment, the second path further includes an optical modulator for controlling a power level of the second laser beam.

These and other features of the present invention are more fully described below in the section titled DETAILED DESCRIPTION OF THE INVENTION.

BRIEF DESCRIPTION OF THE DRAWING FIGURES

The present invention is described herein with reference to the following drawing figures, with greater emphasis being placed on clarity rather than scale.

DETAILED DESCRIPTION OF THE INVENTION

Figure 1:
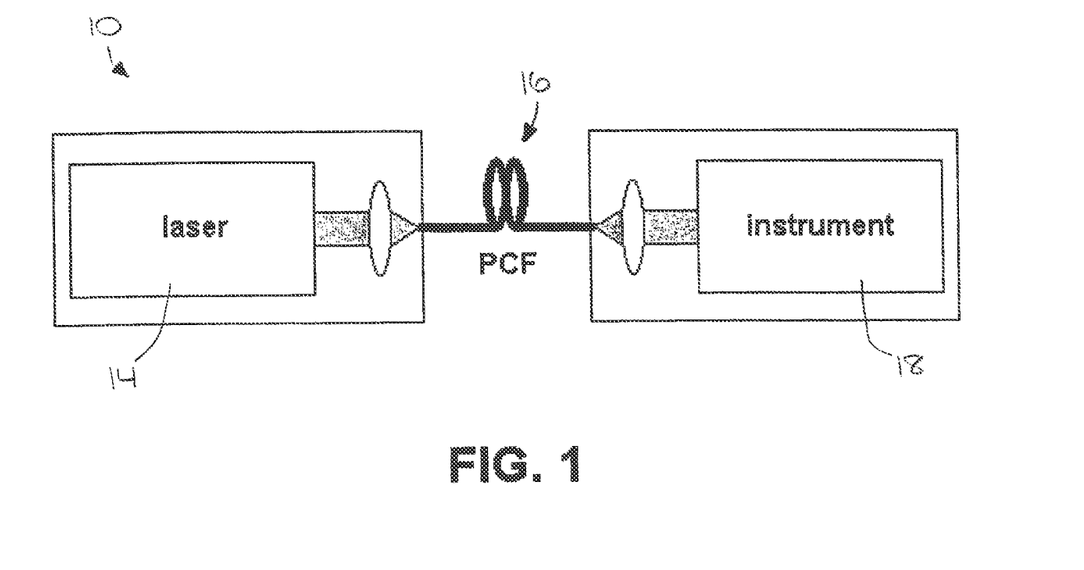
FIG. 1 is a high-level diagram of an embodiment of the laser system of the present invention connected to a photonic excitation investigation instrument.

With reference to the drawings figures, a laser system 10 and methods of using the laser system 10 are herein described, shown, and otherwise disclosed in accordance with various embodiments, including a preferred embodiment, of the present invention. Broadly, the laser system 10 has application in photonic excitation investigation of a target object, in which the target object absorbs the incident photons and emits a corresponding photon which is detected and used to generate an image of the target object. Referring to FIG. 1, in one embodiment, the laser system 10 broadly comprises a laser 14 connected to a non-linear PCF 16 which is, in turn, connected to an instrument 18, such as a two-photon microscope or optical system. Depending on the particular application, e.g., two-photon microscopy or CARS imaging or spectroscopy, additional components may be needed, as discussed below.

Figure 2:
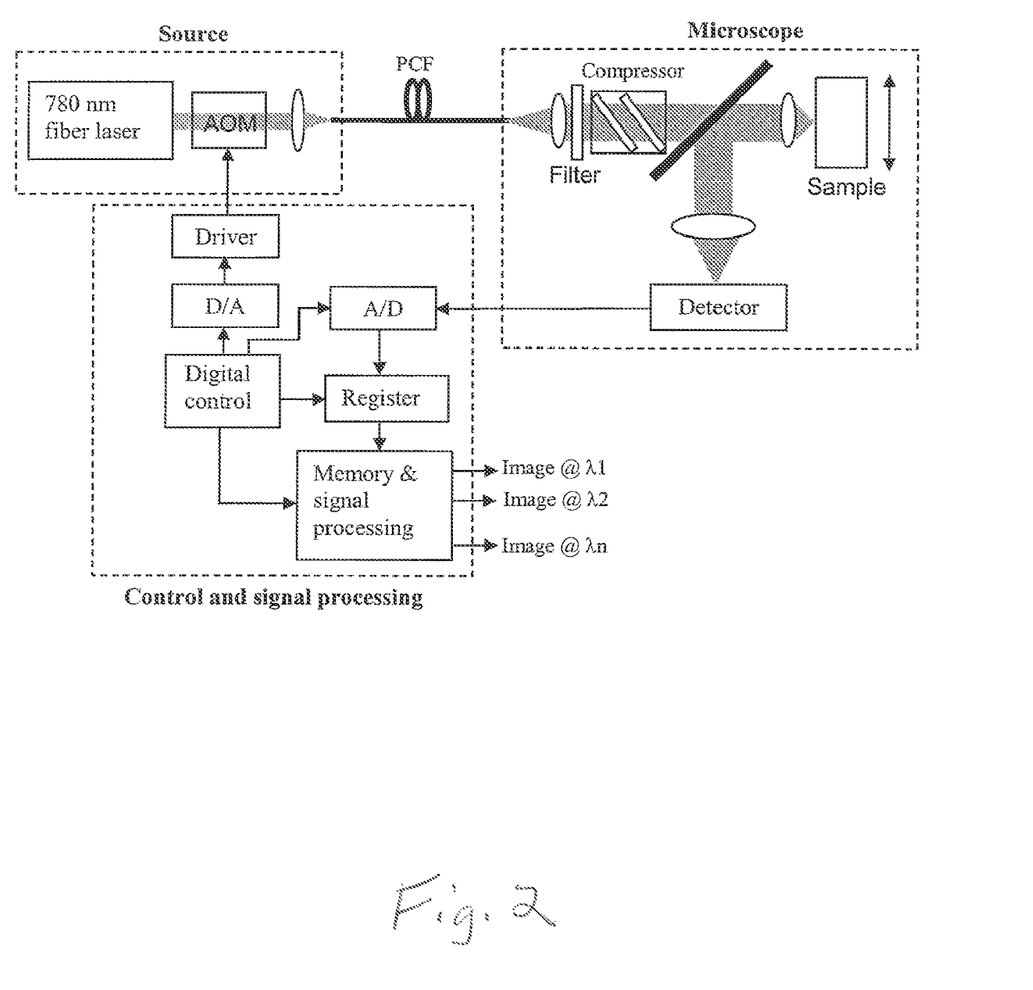
FIG. 2 is a high-level diagram of an embodiment of the laser system incorporated into a two-photon excitation microscopy system.

Referring to FIG. 2, in one embodiment for two-photon microscopy, the laser system 10 is connected to a two-photon microscope 18, which includes a scanning stage 20 and a detector 22, and to control and signal processing components 24.

The laser 14 provides the excitation photons in the form of a beam. In one embodiment, the laser 14 is an ultrafast near-infrared pulsed fiber laser transmitting approximately 100 femtosecond pulses at a wavelength of approximately between 780 nm and 810 nm with a repetition rate of approximately between 50 MHz and 75 MHz and a maximum output power of approximately between 20 mW and 100 mW. However, some or all of these parameters, as well as some or all of the parameters set forth herein for other components of the laser system 10, may change depending on the particular application.

The PCF 16 carries the excitation photons from the laser 14 to the microscope 18. PCFs are sometimes referred to as microstructured fibers (MFs) and microstructured optical fibers (MOFs). In one embodiment, the PCF 16 is of the type referred to as "highly non-linear", or HNL-PCF, which provide a high non-linear coefficient and a positive dispersion parameter in the near-infrared region, allowing for the formation of solitons, or solitary waves. In one embodiment, the PCF 16 is approximately between 6 m and 7 m in length and has a zero dispersion wavelength of 710 nm.

The scanning stage 20 moves, or translates, the target object so as to expose a larger area to the excitation photons. In one embodiment, the scanning stage 20 is a piezo-electric scanning stage. In one embodiment, the scanning stage is replaced by a beam scanner operable to scan the focus of the beam on the target so as to expose a larger area of the target to the excitation photons. The detector 22 detects fluorescence photons emitted by the excited target object, and communicates corresponding electrical signals to the control and signal processing components 24. The control and signal processing components 24 facilitate both controlling the laser 14 and generating images based upon the signals received from the detector 22.

The laser system 10 of the present invention is highly reliable and robust as well as smaller and less expensive than the prior art solid state Ti:Sapphire laser systems. The single fiber coupled laser 14 provides rapid selective two-photon imaging with multiple selectable excitation wavelengths in the near-infrared region, i.e., approximately between 810 nm and 1100 nm, provided by wavelength switching in the PCF 16.

Wavelength switching allows for optimal and selective excitation of multiple fluorophores. More specifically, whereas a single wavelength generally allows for exciting only a specific fluorophore attached to, e.g., a specific protein, a plurality of wavelengths allows for substantially simultaneously exciting a plurality of different fluorophores attached to a plurality of different proteins, and thereby allows for generating a much more informative and comprehensive image of the target object. In the prior art, overlap of the two-photon excitation profiles for different fluorophores has been viewed positively because it allows for simultaneously imaging multiple fluorophores for some combinations of fluorescent dyes. There are, however, applications in which it is beneficial to selectively excite fluorophores. For example, selective excitation allows for rapid image recording at different excitation wavelengths, which permits two-photon excitation of ratiometric fluorescent ion indicators and determination of intracellular $Ca^{2+}$ levels. Similarly, selective excitation allows for unambiguous interpretation of Forster resonance energy transfer (FRET), which permits expanded application of FRET methods in two-photon microscopy.

Wavelength switching in the PCF 16 is accomplished by exploiting the effect of soliton self-frequency shift (SSFS), and does not require altering alignment of the excitation beam into the instrument 18. More specifically, high-power short pulses of laser light propagating within the PCF 16 give rise to an optical soliton. Furthermore, the PCF 16 is capable of generating rapidly wavelength-shifted solitonic radiation with longer infrared wavelengths (approximately >1050 nm), which is not easily accomplished with the prior art Ti:Sapphire laser systems. This capability allows for extending the application of two-photon excitation to flourophores that emit in the red and near-infrared region. The increased transparency of biological tissues to the emission of these dyes makes them desirable for biological imaging.

For the first order soliton produced in a PCF, the peak power, P, the chromatic dispersion of the fiber, D, pulse width, $T_0$, and the non-linearity of the fiber, $\gamma$, are related as follows:

$$\frac{2\pi c \gamma P T_0^2}{\lambda^2 |D(\lambda)|} = 1$$

where D>0 (anomalous dispersion) is required. Because chromatic dispersion generally increases with wavelength, the balance between fiber non-linearity and chromatic dispersion moves toward longer wavelengths with increasing optical power. Therefore, the wavelength of the optical soliton can be changed by adjusting the power launched into the PCF. Conventional optical fibers made for optical communications typically have zero dispersion wavelengths around 1300 nm with positive dispersion slope, and therefore, chromatic dispersion in the approximately 800 nm to 1300 nm region is negative. In this case, an optical soliton will only be produced for excitation wavelengths above 1300 nm. In contrast, a PCF can be designed with a higher level of flexibility. The zero dispersion wavelengths of a PCF can be made as low as approximately 650 nm and the nonlinear coefficient, $\gamma$, can be made two or three orders of magnitude higher than conventional fibers, making it possible to efficiently shift the wavelength of a soliton.

Figure 3:
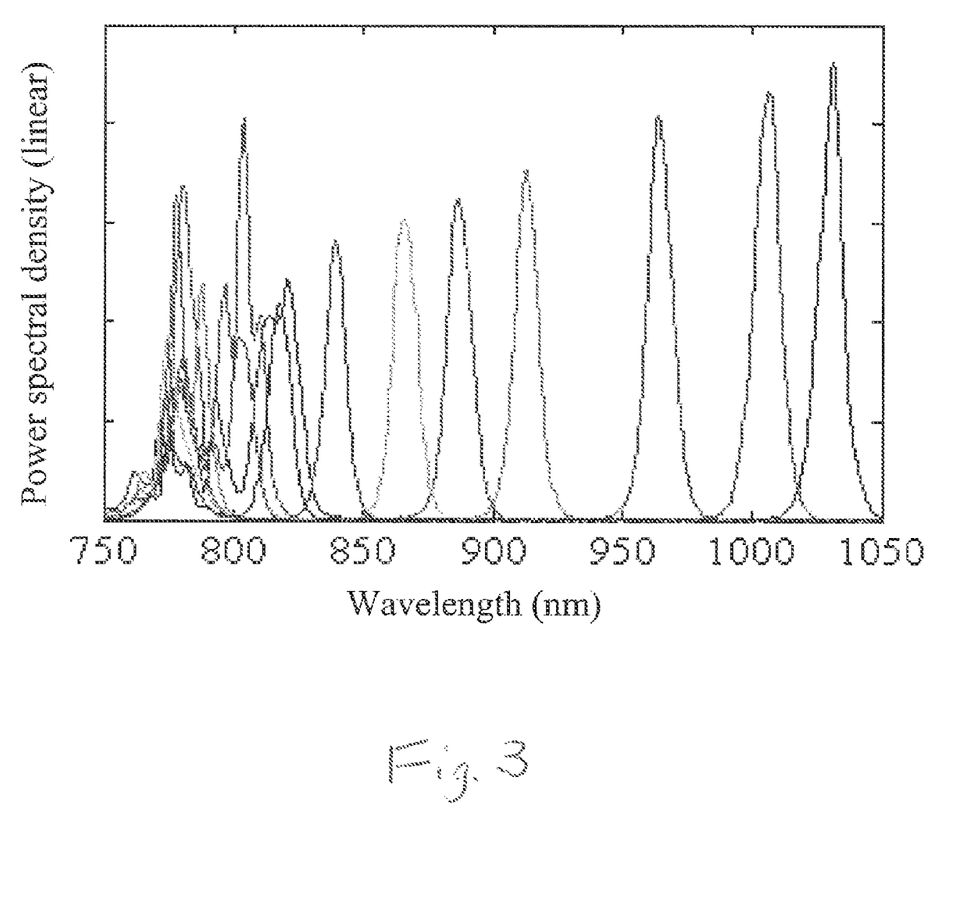
FIG. 3 is a plot of power spectral density versus soliton wavelength, evidencing soliton wavelength shift created by an embodiment of the laser system of FIG. 1.

For the present invention, nonlinear PCF wavelength shifting in the 800 nm wavelength region was confirmed using a 780 nm fiber laser, operating at 20 mW average optical power, coupled into a ~6 m PCF using a 20× objective. For this test, the optical power coupled into the PCF was adjusted by moving the tip of the PCF axially into and out of the focus of the coupling objective. A spectrum analyzer was used to record the resulting spectrum which is shown in FIG. 3. The spectrum demonstrates wavelength shifting from 820 nm to greater than 1035 nm as a function of coupled laser power in the PCF. Unwanted wavelength components, such as those arising from second order soliton creation, can be removed using one or more long-pass filters.

The application of two-photon wavelength switching to biological imaging was demonstrated by imaging bovine pulmonary artery endothelial (BPAE) cells using a 75 MHz, 100 mW fiber laser, generating ultrafast pulses at 810 nm with pulse widths of approximately 100 fsec, coupled into a PCF. In order to adjust the amount of wavelength switching, the laser power coupled into the PCF was attenuated either by a variable neutral density filter before the PCF or by defocusing at the coupling point as described above. For excitation wavelengths shorter than 1000 nm, no second order solution is produced by the PCF, and an 830 nm long-pass color filter was used to reject the remnant light at the original wavelength of the fiber laser. For PCF output wavelengths longer than 1000 nm, a 975 nm long-pass filter was used to reject the second order soliton and other short wavelength components created by the PCF. The cells were imaged with a fluorescent microscope using a data collection system similar to that described above. The sample was raster-scanned across the objective by a piezoelectric scanning stage. A 700 nm short pass dichroic filter was used to reflect the laser beam to the sample and pass the fluorescence to the detector, and a 680 nm short-pass filter was used to filter the excitation beam at the detector.

Figure 4:
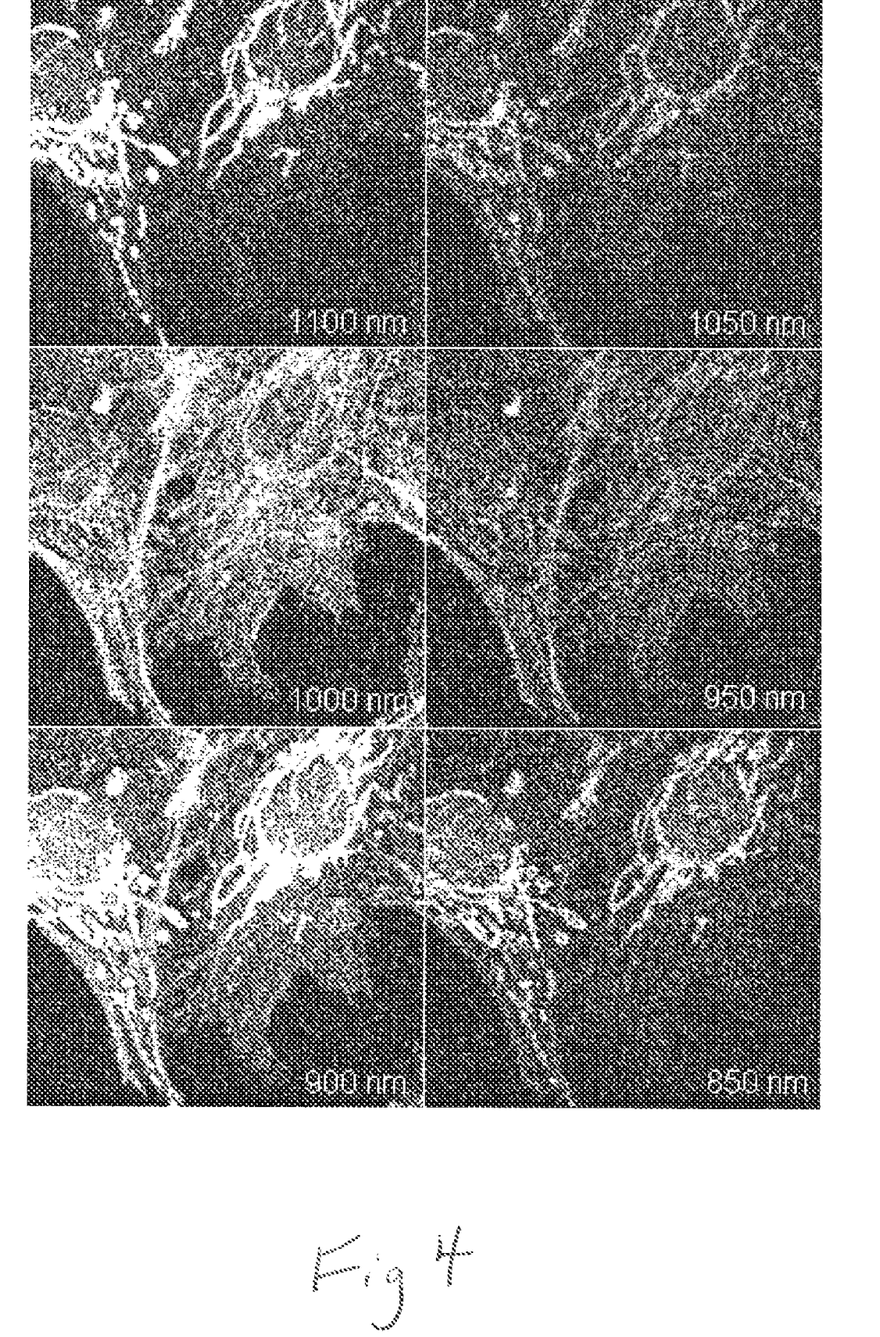
FIG. 4 is a collection of two-photon fluorescence images with two-photon excitation wavelengths from 850 nm to 1100 nm.
Figure 5:
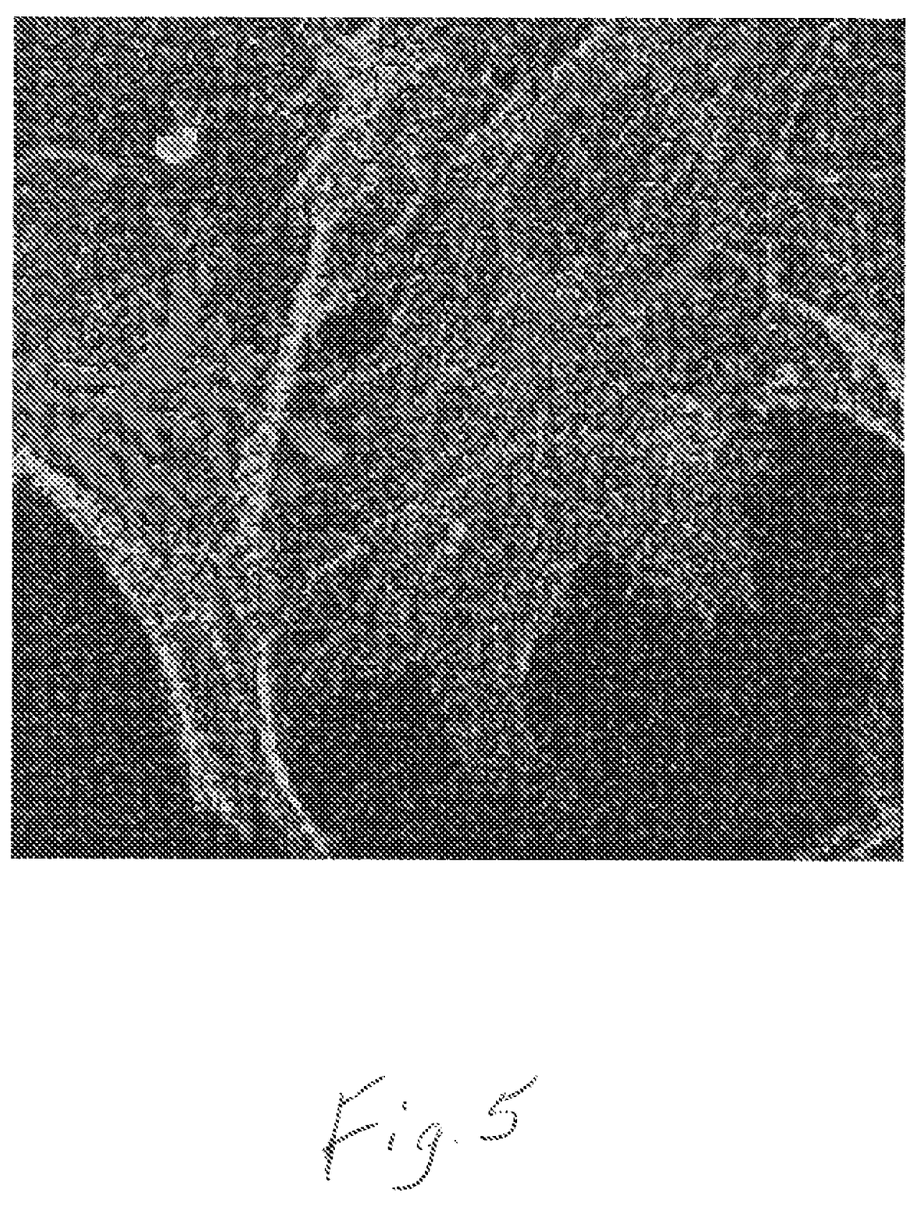
FIG. 5 is a single two-photon fluorescence image which combines two images from FIG. 4 with two-photon excitation wavelengths at 1000 nm and 1100 nm, respectively.
Figure 6:
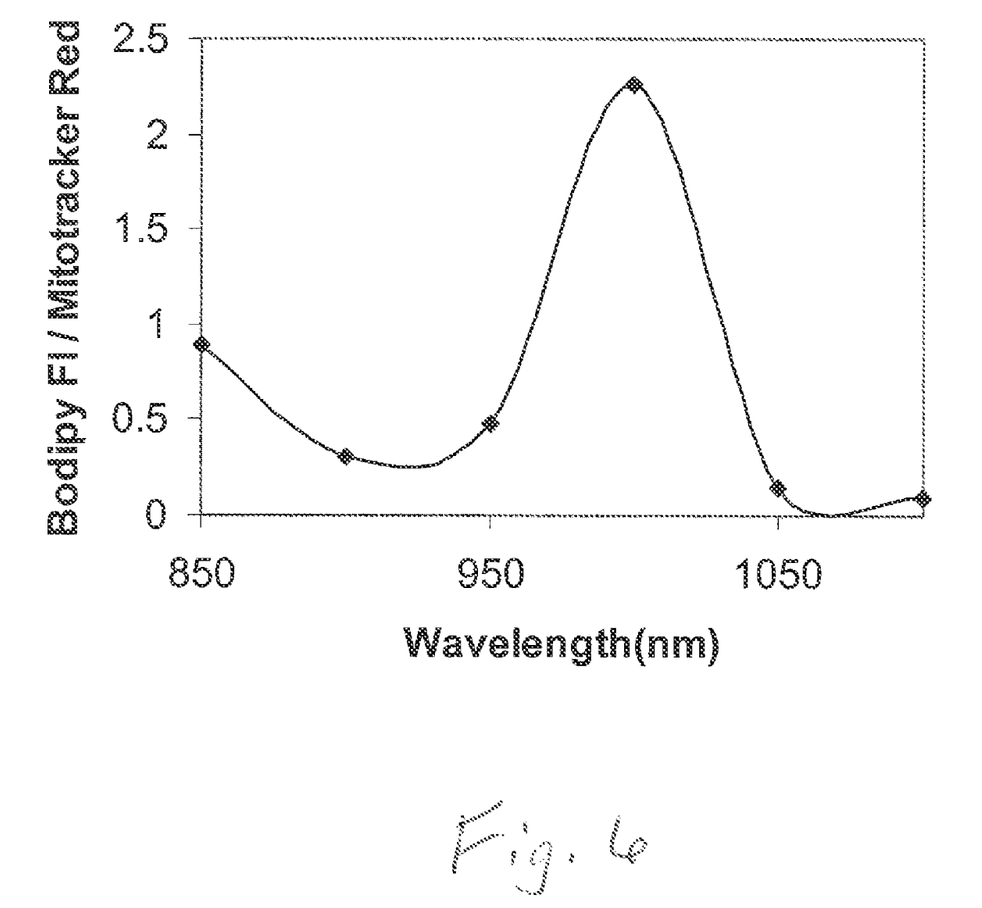
FIG. 6 is a plot of fluorescence intensity versus wavelength.

The resulting images of the BPAE cells are shown in FIG. 4. The mitochondria were stained with MitoTracker Red (a xanthene dye derivative) and the F-actin filaments were stained with Bodipy-F1. FIG. 2 demonstrates clear photoselection of the Bodipy-F1 at 1000 nm and of the MitoTracker Red at 1100 nm. FIG. 5 are false-color images created from the 1000 nm and 1100 nm images demonstrating selective imaging of the F-actin and mitochondrial structures targeted by Bodipy-F1 and MitoTracker Red, respectively. Thus, FIGS. 4 and 5 clearly demonstrate selective two-photon excitation of Bodipy-F1 and MitoTracker Red. FIG. 6 is a plot of the ratio of Bodipy-F1 relative to MitoTracker Red fluorescence intensities as a function of two-photon excitation wavelength. These intensities were selected from areas of the image that contained high concentrations of Bodipy-F1 and MitoTracker Red, respectively.

Comparison of the images of FIG. 3 at 1050 nm and 1100 nm shows that MitoTracker Red was excited much more efficiently at 1100 nm than at 1050 nm. This fluorophore has a maximum excitation wavelength in the visible at 580 nm. Thus, two-photon excitation at 1100 nm likely occurs via the vibronic band of xanthene dyes, which includes fluorescein and tetramethylrhodamine. This band is enhanced in the two-photon excitation spectrum of fluorescein relative to the origin band compared to its relative excitation probability by one-photon excitation. There are a number of dyes having maximum absorption for the lowest excited electronic state in a wavelength range similar to the of Bodipy-F1, i.e., approximately between 450 nm and 500 nm, that can be two-photon excited at approximately between 900 nm and 1000 nm. Additionally, MitoTracker Red is spectrally and structurally similar to several xanthene dyes, e.g., Texas Red, that may also have minima in their excitation spectra in the 1000 nm region. Thus, many dye combinations could be selectively excited by wavelength switching between 1000 nm and 1100 nm using the present invention.

Figure 7:
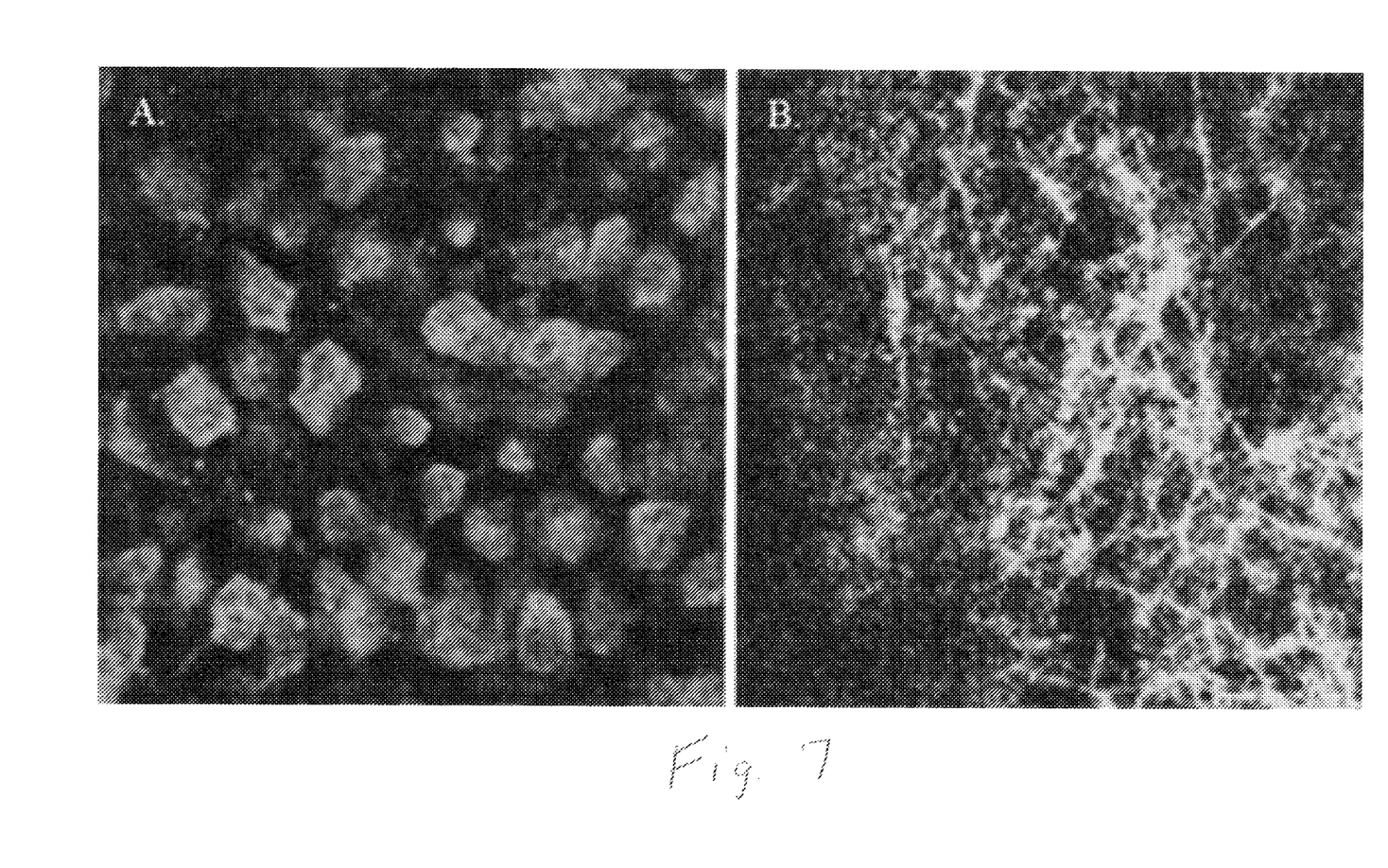
FIG. 7 is a collection of two-photon fluorescence images at 810 nm and 1050 nm.

FIG. 7 further demonstrates the usefulness of the present invention for tissue imaging. These images are of developing vascular tissue in quail embryos in which nuclei were stained with DAPI and fibrillin was stained with Alexa Fluor 555. Each of these images shows a different region of the tissue at 810 nm with the fiber laser without the PCF and at 1050 nm with the PCF. At 810 nm, the nuclei were photoselected, while at 1050 nm the fibrillin structures were observed without interference from the DAPI stained nuclei. As with the BPAE cells discussed above, photoselection was accomplished by switching the excitation to a wavelength longer than the lowest energy excited state of the blue-absorbing chromophore.

Figure 8:
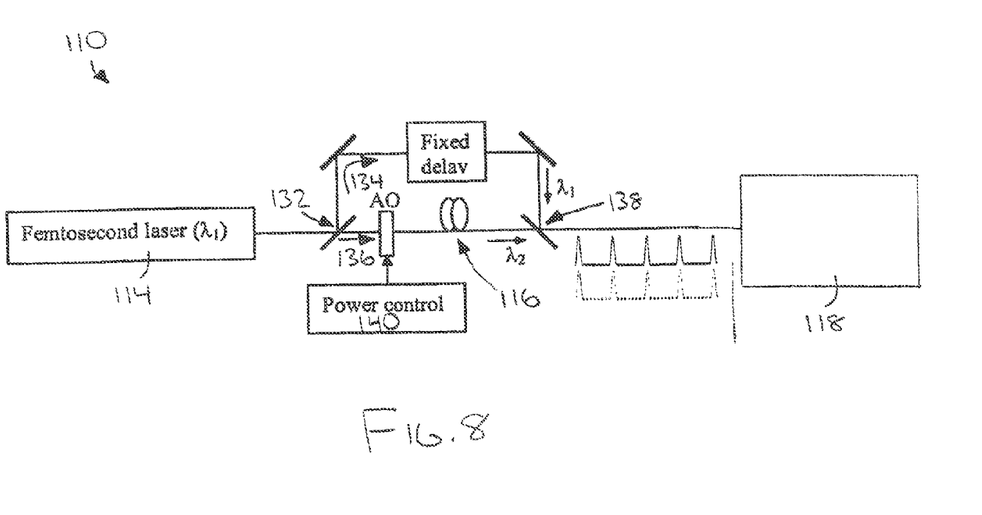
FIG. 8 is a high-level diagram of an embodiment of the laser system incorporated into a CARS imaging or spectroscopy system.

When adapted for coherent Raman imaging or spectroscopy, the laser system of the present invention allows for using a single fiber laser in place of the two different, expensive, and stringently synchronized solid state lasers conventionally used in this technique. Referring to FIG. 8, in one embodiment for CARS imaging or spectroscopy, the laser system 110 includes the laser 114, a beam splitter 132, a first path 134 and a second path 136, and a beam combiner 138, and is connected to a spectroscope 118. The first path 134 introduces an optical delay. The second path includes a mechanism for varying light intensity, such as an optical modulator 140, and the PCF 116.

Figure 9:
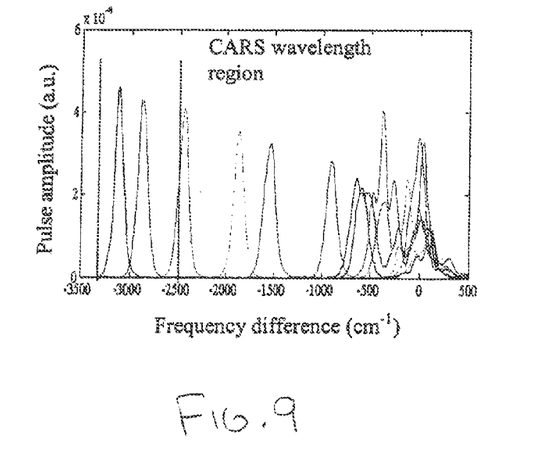
FIG. 9 is a plot of pulse amplitude versus frequency difference.

The beam splitter 132 splits the output of the laser 114 into two substantially identical beams; the first beam travels along the first path 134 and the second beam travels along the second path 136. The second beam passes through the optical modulator 140 and is injected into the PCF 116. As a result of SSFS introduced by Raman scattering and Kerr-effect non-linearity, the second beam is shifted to a longer wavelength. The amount of shift depends on the optical power level injected into the PCF 116, which is controlled by the optical modulator 140. The optical delay introduced in the first path 134 matches the delay introduced by wavelength shifting in the second path 136. Because the two beams are generated by the same laser 114, their repetition rate is identical and therefore, no active stabilization circuit is required. Referring to FIG. 9, a plot of pulse amplitude versus frequency difference reveals the wavelength shift in the region of interest for CARS imaging or spectroscopy.

Although the invention has been disclosed with reference to various particular embodiments, it is understood that equivalents may be employed and substitutions made herein without departing from the scope of the invention as recited in the claims.

Having thus described the preferred embodiment of the invention, what is claimed as new and desired to be protected by Letters Patent includes the following:

1. A laser system for use in coherent Raman imaging or spectroscopy, the laser system comprising:
   a pulsed fiber laser operable to produce an output laser beam;
   a beam splitter operable to split the output laser beam into a first laser beam and a second laser beam;
   a first path operable to carry the first laser beam;
   a second path operable to carry the second laser beam, the second path including a non-linear photonic crystal fiber operable to shift a wavelength of the second laser beam,
   wherein the first path introduces an optical delay to the first laser beam which substantially matches a delay introduced by wavelength-shifting the second laser beam; and
   a beam combiner operable to recombine the first laser beam and the second laser beam.

2. The laser system as set forth in claim 1, wherein the second path further includes an optical modulator for controlling a power level of the second laser beam.

3. In a system for performing coherent Raman imaging or spectroscopy on a target object, the system including a laser system and an imaging or spectroscopy instrument, the improvement comprising:
   the laser system including—
      a pulsed fiber laser operable to produce an output laser beam;
      a beam splitter operable to split the output laser beam into a first laser beam and a second laser beam;
      a first path operable to carry the first laser beam;
      a second path operable to carry the second laser beam, the second path including a non-linear photonic crystal fiber operable to shift a wavelength of the second laser beam,
      wherein the first path introduces an optical delay to the first laser beam which substantially matches a delay introduced by wavelength-shifting the second laser beam; and
      a beam combiner operable to recombine the first laser beam and the second laser beam,
      wherein the recombined first laser beam and second laser beam are provided to the imaging or spectroscopy instrument.

4. The laser system as set forth in claim 3, wherein the second path further includes an optical modulator for controlling a power level of the second laser beam.

5. A system utilizing coherent Raman scattering to produce an image or spectrograph of a target object, the system comprising:
   a laser system including—
      a pulsed fiber laser operable to produce an output laser beam;
      a beam splitter operable to split the output laser beam into a first laser beam and a second laser beam;
      a first path operable to carry the first laser beam;
      a second path operable to carry the second laser beam, the second path including a non-linear photonic crystal fiber operable to shift a wavelength of the second laser beam,
      wherein the first path introduces an optical delay to the first laser beam which substantially matches a delay introduced by wavelength-shifting the second laser beam;
      a beam combiner operable to recombine the first laser beam and the second laser beam; and
   an imaging or spectroscopy instrument operable to receive the recombined first and second laser beams from the non-linear photonic crystal fiber and direct them toward the target object.

6. The system as set forth in claim 5, wherein the second path further includes an optical modulator for controlling a power level of the second laser beam.

7. A method of performing coherent Raman imaging or spectroscopy, the method comprising the steps of:
   generating an output laser beam using a pulsed fiber laser;
   splitting the output laser beam into a first laser beam and a second laser beam;
   carrying the first laser beam on a first path;
   carrying the second laser beam on a second path and shifting a wavelength of the second laser beam using a non-linear photonic crystal fiber, wherein the first path introduces an optical delay to the first laser beam which substantially matches a delay introduced by wavelength-shifting the second laser beam;
   recombining the first laser beam and the second laser beam; and
   delivering the recombined first and second laser beams to an imaging or spectroscopy instrument.

8. The method as set forth in claim 7, further including the step of controlling a power level of the second laser beam using an optical modulator.

* * * * *

UNITED STATES PATENT AND TRADEMARK OFFICE
CERTIFICATE OF CORRECTION

| | |
|---|---|
| PATENT NO. | : 7,525,724 B2 |
| APPLICATION NO. | : 11/687162 |
| DATED | : April 28, 2009 |
| INVENTOR(S) | : Rongqing Hui and Carey K. Johnson |

It is certified that error appears in the above-identified patent and that said Letters Patent is hereby corrected as shown below:

On the title page item (75) "Inventors:", delete the name "Rongqui" and insert

--Rongqing-- as the correct spelling of the name of the first inventor is Rongqing HUI.

Signed and Sealed this

Sixteenth Day of June, 2009

JOHN DOLL
*Acting Director of the United States Patent and Trademark Office*